United States Patent [19]

Riley, Jr.

[11] 4,309,067

[45] Jan. 5, 1982

[54] MECHANICAL AND ELECTRICAL CONNECTION INTERFACE FOR A BATTERY CONTAINING PACK

[75] Inventor: Robert H. Riley, Jr., Towson, Md.

[73] Assignee: Black & Decker Inc., Newark, Del.

[21] Appl. No.: 86,026

[22] Filed: Oct. 17, 1979

[51] Int. Cl.³ .......................................... H01R 13/639
[52] U.S. Cl. .................................. 339/91 R; 339/152
[58] Field of Search ............................. 339/91 R, 152

[56] References Cited

U.S. PATENT DOCUMENTS 3,973,179  8/1976  Weber et al. ................. 339/91 R X
4,113,337  9/1978  McKee ............................. 339/91 R

*Primary Examiner*—Eugene F. Desmond
*Attorney, Agent, or Firm*—Harold Weinstein; Walter Ottesen; Edward D. Murphy

[57] ABSTRACT

A connection interface for mechanically and electrically connecting a battery containing pack and a battery utilizing device includes a plurality of outwardly facing lugs positioned on the battery pack to define outwardly facing tab-receiving slots. Cooperating inwardly facing tabs located on the battery utilizing device define inwardly facing lug-receiving slots such that the outwardly facing lugs are received within the inwardly facing lug-receiving slots and the inwardly facing tabs are received within the outwardly facing tab-receiving slots. The mating faces of the tabs and lugs are inclined relative to a medial plane to accomodate accumulated tolerances and assist in providing a rigid mechanical connection. A manually operable latch is provided to prevent unintentional separation of the battery pack and the battery utilizing device.

7 Claims, 8 Drawing Figures

U.S. Patent  Jan. 5, 1982  4,309,067
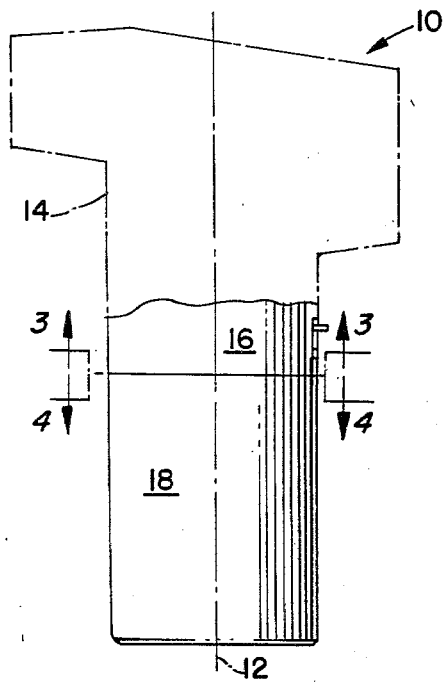
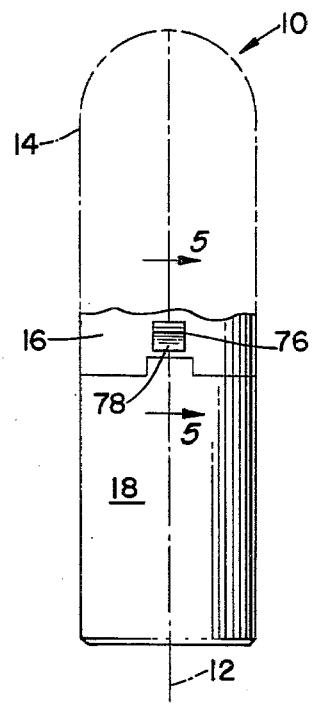
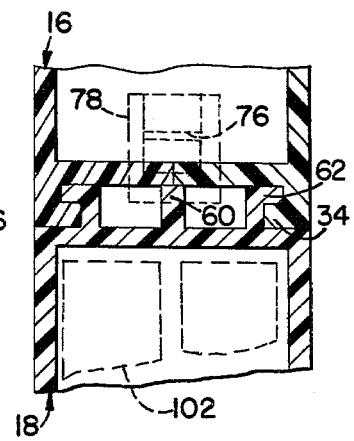
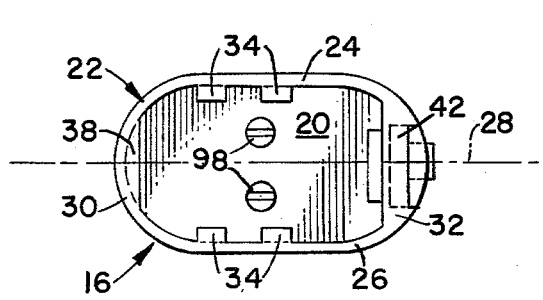
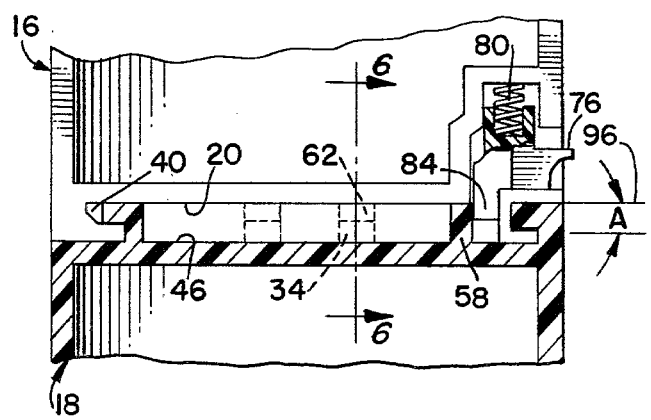
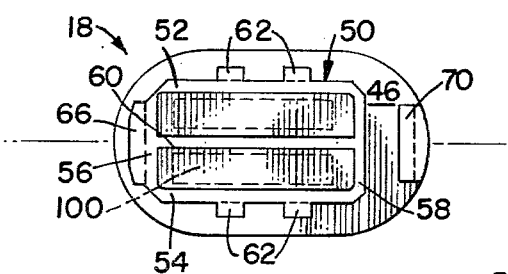
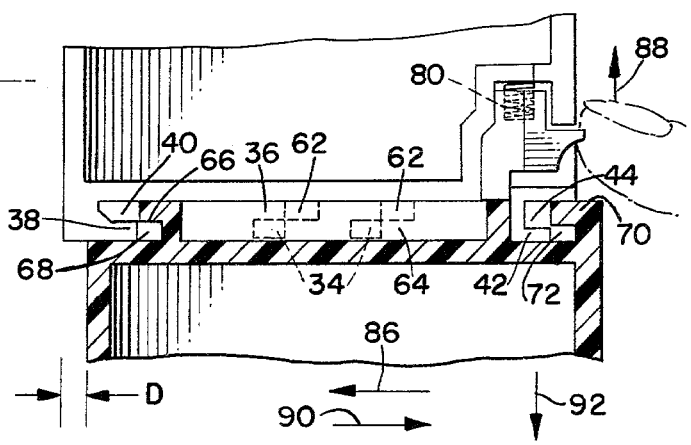
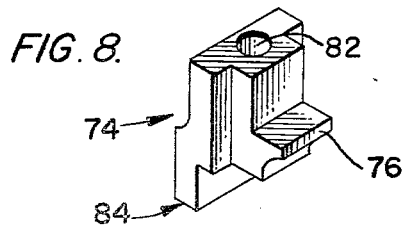

MECHANICAL AND ELECTRICAL CONNECTION INTERFACE FOR A BATTERY CONTAINING PACK

BACKGROUND OF THE INVENTION

The present invention relates to a connection interface for connecting a battery containing pack with a battery utilizing device, and, more particularly, to a connection interface for effecting both a structurally rigid mechanical interconnection and a reliable electrical interconnection between a battery containing pack and a battery utilizing device.

Portable battery-powered tools, such as portable electric drills, typically include a battery formed from a plurality of rechargeable secondary cells that are permanently installed within the tool housing. The battery is recharged with a battery charger through an electrical connector on the tool. Such tools may be used until their battery is discharged after which the tool must be connected to its accompanying charge to effect replenishment of the battery. During the recharging period, the tool is normally not available for portable use. While this battery/tool arrangement is suitable for a wide variety of applications, it presents a problem with respect to medical applications, especially surgical applications, in which recharging of the battery during surgery is impracticable. While it is possible to provide battery receiving cavities in the tool housing to permit battery replacement, the manual removal of the depleted battery and replacement with a freshly charged battery can be time consuming, especially in the case where a plurality of individual cells must be replaced.

SUMMARY OF THE INVENTION

Accordingly, it is a broad overall object of the present invention among others to provide a connection interface for connecting a battery containing pack with a battery utilizing device in which both a mechanical and an electrical connection is effected.

It is another object of the present invention to provide a connection interface for connecting a battery containing pack with a battery utilizing device in which both the battery pack and the battery utilizing device, when connected, are structurally integrated to provide a rigid mechanical interconnection.

It is still a further object of the present invention to provide a connection interface for connecting a battery pack and a battery utilizing device in which the battery pack defines part of the device handle and is adapted to be connected through the connection interface to a handle stub to provide a structurally integrated handle.

It is still another object of the present invention to provide a connection interface for a battery pack and a battery utilizing device in which the battery pack can be unlatched and removed from the device by a simple one-handed manipulation.

A connection interface for a battery pack and a battery utilizing device in accordance with the present invention includes tabs that extend upwardly from a base surface of a battery pack and complementary lugs that extend downwardly from a base surface of the battery utilizing device such that the tabs define lug-receiving spaces or slots and the lugs define tab-receiving spaces or slots relative to their respective base surfaces. When connected, the lugs of the battery utilizing device are received within the lug-receiving slots defined by the tabs, and the tabs of the battery pack are received within the tab-receiving slots defined by the lugs. The contacting surfaces of the lugs and tabs are inclined relative to a medial plane to permit the tab/lug interconnection to take-up and accomodate accumulated clearances and thereby provide a structurally rigid connection between the battery pack and the battery utilizing device. A finger operated latch is provided to permit the battery pack to be unlatched from and separated from the battery utilizing device. In the preferred embodiment, the battery pack is formed as part of a handle extension for a portable electric drill intended for medical applications so that the battery pack, when connected to a handle stub portion of the drill, is structurally integrated with the stub to provide a rigid, structurally integrated handle for the tool. The connection interface permits the battery pack to be quickly connected and disconnected from the electric drill with disconnection effected by a simple one-handed manipulation.

DESCRIPTION OF THE FIGURES

The above description, as well as the objects, features, and advantages of the present invention will be more fully appreciated by reference to the following detailed description of a presently preferred but nonetheless illustrative embodiment in accordance with the present invention when taken in conjunction with the accompanying drawings wherein:

FIG. 1 is a side elevational view of a battery-powered electric drill connected to a handle-type battery pack;

FIG. 2 is a rear elevational view of the battery-powered electric drill and battery pack shown in FIG. 1;

FIG. 3 is a bottom view of a connection interface portion of the electric drill taken along line 3—3 of FIG. 1;

FIG. 4 is a top view of a connection interface portion of the battery pack taken along line 4—4 of FIG. 1;

FIG. 5 is an enlarged side elevational view, in cross section, of the connected electric drill and the battery pack taken along line 5—5 of FIG. 2;

FIG. 6 is an enlarged rear elevational view, in cross section, of the connected electric drill and battery pack taken along line 6—6 of FIG. 5;

FIG. 7 is an enlarged side elevational view, similar to that of FIG. 5, of the connected electric drill and battery pack showing a finger-operated latch in an unlatching position and the battery pack partially disengaged from the electric drill; and FIG. 8 is a detailed perspective view of a finger-operated latch used to selectively latch the battery pack to the electric drill.

DESCRIPTION OF THE PREFERRED EMBODIMENT

A connection interface in accordance with the present invention is shown in the figures in combination with a battery-powered electric drill that is generally designated by the reference character 10. As shown in FIGS. 1 and 2, the electric drill 10 is formed generally about a vertically aligned tool axis 12 and includes a power head 14 (shown in partial broken-line illustration) that contains an electrically driven motor and a gear head (not shown) and a handle stub 16 that is designed to be mechanically and electrically interconnected with a battery pack 18 so that the handle stub 16 and the battery pack 18 constitute a structurally integrated tool handle. As described in more detail below, both the electric drill 10 and the battery pack 18 have confronting base surfaces that are provided with complementary lugs and tabs that inter-engage to effect the mechanically rigid connection.

As shown in FIG. 3, the bottom of the handle stub 16 is provided with a base surface 20 that includes a rim 22 formed on the periphery of the base surface 20 with the rim 22 extending downwardly from the base surface 20 in FIG. 1. The rim 22 defines side walls 24 and 26 formed on opposite sides of a longitudinally aligned axis 28, a curved forward wall portion 30, and a curved rearward wall portion 32.

A pair of lugs 34 are formed on the rim 22 on each side wall 24 and 26. The lugs 34 extend inwardly from their respective side walls toward each other and toward the longitudinal axis 28. Each of the lugs 34 is spaced from the base surface 20 of the electric drill 10 to define a tab-receiving space or slot 36 therebetween (see FIG. 7).

A rearwardly facing flange or tongue 38 is provided on the curved forward wall 30 of the rim 22 and is spaced from the base surface 20 to define a rearwardly facing projection-receiving slot 40 (see FIGS. 5 and 7) that is aligned substantially laterally to the longitudinal axis 28. As second rearwardly facing flange or tongue 42 is provided on the curved rearward wall 32 of the rim 22 and is likewise spaced from the base surface 20 and spans on an open portion of the rear wall 32 to define a second rearwardly facing projection-receiving slot 44 (see FIG. 7).

The battery pack 18, as shown in FIG. 4 includes a base surface 46 and a wall 50 that extends upwardly from the base surface. The wall 50 describes a generally open rectangle that includes two side walls 52 and 54, a forward wall 56, a rear wall 58, and an intermediate wall 60 that is aligned along the longitudinal axis 28 as shown in FIG. 4.

A pair of tabs 62 are formed on each of the side walls 52 and 54 and extend from their respective wall portions in opposite directions from one another and outwardly of the longitudinal axis 28. The tabs 62 on each side wall are spaced from one another along the longitudinal axis 28 approximately the same distance as the lugs 34 of the electric drill 10 and are also spaced above the base surface 46 to define lug-receiving spaces or slots 64 therebetween (see FIG. 7). A forwardly facing projection 66 is formed on the forward wall 56 and is laterally aligned relative to the longitudinal axis 28. The projection 66 is spaced above the base surface 46 to define a forwardly facing tongue-receiving slot or space 68 therebetween (see FIG. 7). A second forwardly facing projection 70 is provided on the rearmost portion of the base surface 46 of the battery pack 18 and is laterally aligned relative to the longitudinal axis 24. The projection 70 is also spaced above the base surface 46 to define a second forwardly facing tongue-receiving slot 72 therebetween (see FIG. 7).

A finger-operated latch 74, as shown in detail in FIG. 8, is provided in the handle stub 16 of the electric drill 10 to permit the electric drill and the battery pack 18 to be latched and unlatched from one another. The latch 74 includes a finger-operated trigger 76 that extends through a generally rectangular slot 78 (FIG. 2) formed in the rear wall portion of the handle stub 16. The latch 74 is retained in an appropriately shaped cavity in the handle stub 16 and is resiliently urged in a downward direction by a helical spring 80, in compression, (FIG. 5) retained in a counterbore 82 formed in the upper portion of the latch 74. A stem 84 extends downwardly from the latch 74 and is designed to latch the battery pack 18 in place as described more fully below.

In order to connect the battery pack 18 and the electric drill 10, the battery pack 18 is positioned, as shown in FIG. 7, immediately below the handle stub 16 of the electric drill 10 with the open rectangle defined by the wall 50 inserted into the opening defined by the rim 22 of the handle stub 16. The battery pack 18 is initially offset rearwardly of the handle stub 16 as indicated by the distance "D" in FIG. 7 such that the first and second rearwardly facing tongues 38 and 42 of the handle stub 16 are positioned immediately adjacent to and aligned with their respective forwardly facing tongue-receiving spaces 68 and 72 of the battery pack 18; the first and second forwardly facing projections 66 and 70 of the battery pack 18 are positioned immediately adjacent to and aligned with the rearwardly facing projection-receiving spaces 40 and 44 of the handle stub 16; and the lugs 34 of the handle stub 16 and the tabs 62 of the battery pack 18 are positioned immediately adjacent to and aligned with their respective lug-receiving slots 64 and their respective tab receiving slots 36. The battery pack 18 is then pushed in a forward direction as indicated by the arrow 86 in FIG. 8 to cause the various tongues, projections, lugs, and tabs to enter their respective receiving slots. Thus, when the electric drill 10 and the battery pack 18 are interconnected, as shown in FIG. 5, the tongues 38 and 42 are received within their respective receiving slots 68 and 72, the projections 66 and 70 are received within their respective projection-receiving slots 40 and 44, and the lugs 34 and the tabs 62 are received within their respective lug-receiving slots 64 and tab-receiving slots 36.

When the battery pack 18 and the electric drill 10 are interconnected, the stem 84 portion of the latch 74 is resiliently urged downward by the spring 80 and enters the space defined between the rear wall 58 of the battery pack 18 and the forwardly facing projection 70 of the electric drill 10 to latch the battery pack in place.

In order to disconnect or separate the battery pack 18 from the electric drill 10, as shown in FIG. 7, the finger-operated trigger 76 is pushed in an upward direction as indicated by the arrow 88 against the resiliency of the spring 80 to cause the locking stem 84 of the latch 74 to move upwardly above the rear wall 58 of the battery pack 16. The battery pack 18 is then pulled rearwardly relative to the electric drill 10 as indicated by the arrow 90 until the various tongues, projections, lugs, and tabs clear one another. Thereafter the battery pack 18 is separated from the electric drill 10 by pulling it downwardly in the direction of the arrow 92. As can be appreciated, the separation may be effected by a one-handed manipulation in that the thumb may be used to urge the finger-operated trigger 76 upwardly while the first two fingers of the hand grip the handle stub 16 and the remaining two fingers grip the battery pack 18 to pull it rearwardly and downwardly during separation.

The various lugs, tabs, projections and tongues are designed so that the mating or contacting surfaces fit together with a line-to-line fit. Preferably, the mating or contacting surfaces of the various lugs, tabs, tongues, and projections are inclined relative to a medial reference plane 96 (FIG. 5) that contains the longitudinal axis 28 and that is generally normal to the vertical axis 12 of the tool 10. As shown in FIG. 5, each of the mating or contacting surfaces are inclined by an angle A (for example 1°) to the medial plane such that the forward most projection is somewhat thinner than the rearmost projection. The inclination of the various mating or contacting surfaces permits the connection interface to take-up or accomodate accumulated tolerances to provide a clearance-free mechanically rigid interconnection between the battery pack 16 and the electric drill 10.

Electrical contact between the battery pack 18 and the electric drill 10 is effected by electrical contacts located on the base surfaces 20 and 46 of the battery pack and electric drill. In the preferred embodiment, the electric drill 10 is provided with silver plated button-head screws 98 on its base surface 20 that are connected to the electric motor within the power head. The battery pack 18 includes two silver plated, resilient leaf springs 100 (broken-line illustration) that are aligned parallel to the longitudinal axis 28 and that are connected to rechargeable secondary cells 102 (broken-line illustration in FIG. 6) within the battery pack housing.

As will be apparent to those skilled in the art, various changes and modifications may be made to the connection interface of the present invention without departing from the spirit and scope of the invention as recited in the appended claims and their legal equivalent.

What is claimed is:

1. A dual-motion separable connection interface, having a first longitudinal axis, for connecting a battery-containing pack with a battery utilizing device, having a second axis, said connection interface comprising:

a plurality of rigid tabs connected to a base surface of said battery-containing pack, two of said tabs being separated from each other along said first longitudinal axis by a tab space and positioned on each opposite side of said first longitudinal axis, said two tabs directed laterally outwardly a first uniform distance from said longitudinal axis and spaced from said base surface of said battery pack to define lug-receiving slots therebetween;

a plurality of rigid lugs connected to a base surface of said battery utilizing device, two of said lugs separated from each other along said first longitudinal axis by a lug space and positioned on each opposite side of said first longitudinal axis, said two lugs directed laterally inwardly and being spaced a second uniform distance from said longitudinal axis, and being further spaced from said base surface of said battery pack to define tab-receiving slots therebetween;

locking means for preventing motion along said first longitudinal axis of said battery pack relative to said battery utilizing device to prevent separation thereof, said locking means including a movable stem mounted on said battery utilizing device and means for biasing said stem outwardly towards said battery-containing pack from a first position to a second position;

said locking means further including a rigid abutment operatively associated with said stem and connected to, and extending outwardly from said battery-containing pack towards said battery utilizing device;

one of said two tabs being received in one of said lug spaces, one of said two lugs being received in one of said tab spaces, and said abutment moving said stem from said second position inwardly to said first position, when said battery-containing pack is moved towards said battery utilizing device in a direction parallel to said second axis to initiate connection;

said tabs being received in said tab receiving slots, said lugs being received in said lug-receiving slots, and said stem moving from said first position to said second position when said battery-containing pack is moved away from said stem in a direction parallel to said first longitudinal axis to complete connection; and said battery-containing pack and said battery utilizing device being separable by relative motion therebetween parallel to said first longitudinal axis, followed by relative motion therebetween parallel to said second axis.

2. The separable connection interface claimed in claim 1, further comprising:

a projection connected to said base surface of said battery pack transverse to said longitudinal axis and facing in a forward direction, said projection spaced from said base surface of said battery pack to define a tongue-receiving slot therebetween;

a rearwardly facing tongue connected to the base surface of said battery utilizing device transverse to said longitudinal axis, said tongue spaced from said base surface of said battery utilizing device to define a projection-receiving slot therebetween whereby said projection and said tongue, when said battery pack and said battery utilizing device are connected, are received, respectively, within said projection-receiving slot and said tongue-receiving slot.

3. The connection interface claimed in claim 2 further comprising:

a second projection connected to said base surface of said battery pack transverse to said longitudinal axis and facing in a forward direction, said second projection spaced from said base surface of said battery pack to define a second tongue-receiving slot therebetween;

a second rearwardly facing tongue connected to the base surface of said battery utilizing device transverse to said longitudinal axis, said tongue spaced from said base surface of said battery utilizing device to define a second projection receiving slot therebetween whereby said second projection and said second tongue, when said battery pack and said battery utilizing device are connected, are received, respectively, within said second projection-receiving slot and said second tongue-receiving slot.

4. The connection interface claimed in claim 2 wherein the mating surfaces of said tabs and lugs are inclined relative to a medial plane of said connection interface.

5. The connection interface claimed in claim 1 wherein said battery pack comprises the handle portion of said battery utilizing device.

6. The connection interface claimed in claim 1, further comprising:

electrical contacts located on said battery pack and electrical contacts located on said battery utilizing device, said contacts making mutual contact with one another when said battery pack and said battery utilizing device are connected.

7. The connection interface claimed in claim 6, wherein said electrical contacts of said battery pack comprising:

electrically conductive resilient leaf springs mounted on said base surface of said battery pack and aligned substantially parallel to said longitudinal axis of said connection interface.

* * * * *